United States Patent [19]

Haugwitz

[11] 4,338,435
[45] Jul. 6, 1982

[54] BENZOTHIADIAZINES HAVING DIURETIC ACTIVITY

[75] Inventor: Rudiger D. Haugwitz, Titusville, N.J.

[73] Assignee: E. R. Squibb & Sons, Inc., Princeton, N.J.

[21] Appl. No.: 268,944

[22] Filed: Jun. 1, 1981

[51] Int. Cl.$^3$ .................. C07D 285/30; C07D 285/24
[52] U.S. Cl. .......................... 544/13; 544/6; 544/12
[58] Field of Search .............................. 544/6, 12, 13

[56] References Cited

U.S. PATENT DOCUMENTS 3,102,882  9/1963  McMannus et al. ................ 544/13
3,287,215  11/1966  Robertson et al. ................ 544/13
3,311,620  3/1967  Bell et al. ............................. 544/13
4,025,508  5/1977  Perrault ............................... 544/12

FOREIGN PATENT DOCUMENTS 930671  7/1963  United Kingdom .................. 544/6

OTHER PUBLICATIONS

Merck Index, ninth edition, Windholz et al. editors, 1976; items 312, 1042, 4668 and 7362.

Primary Examiner—John M. Ford
Attorney, Agent, or Firm—Lawrence S. Levinson; Donald J. Barrack

[57] ABSTRACT

Compounds having the formula

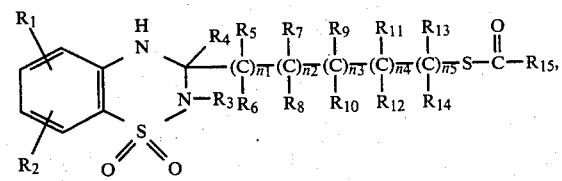

wherein $R_1$ and $R_2$ are each independently hydrogen, halogen, trifluoromethyl, aminosulfonyl, nitro, alkyl or alkoxy;

$R_3$ is hydrogen, alkyl, or phenylmethyl;

$R_4$ is hydrogen, alkyl, or phenyl, and $R_{15}$ is alkyl, phenyl or phenylmethyl, or $R_4$ and $R_{15}$ together are $-(CH_2)_m-$ wherein m is 1 or 2;

$R_5, R_6, R_7, R_8, R_9, R_{10}, R_{11}, R_{12}, R_{13}$ and $R_{14}$ are each independently hydrogen, halogen, alkyl or phenyl;

$n_1, n_2, n_3, n_4$ and $n_5$ are each independently 0 or 1;

with the proviso that if $R_4$ and $R_{15}$ together are $-(CH_2)_m-$ the sum of $n_1, n_2, n_3, n_4, n_5$ and m is 2 or 3;

have diuretic activity.

9 Claims, No Drawings

BENZOTHIADIAZINES HAVING DIURETIC ACTIVITY

BRIEF DESCRIPTION OF THE INVENTION

Compounds having the structural formula

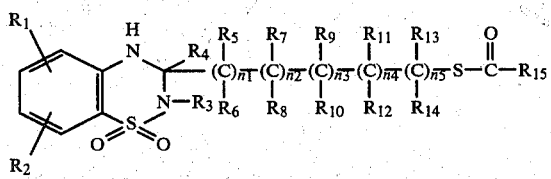

have diuretic activity. In formula I, and throughout the specification, the symbols are as defined below.

$R_1$ and $R_2$ are each independently hydrogen, halogen, trifluoromethyl, aminosulfonyl, nitro, alkyl or alkoxy;

$R_3$ is hydrogen, alkyl, or phenylmethyl;

$R_4$ is hydrogen, alkyl, or phenyl, and $R_{15}$ is alkyl, phenyl or phenylmethyl, or $R_4$ and $R_{15}$ together are $-(CH_2)_m-$ wherein m is 1 or 2;

$R_5$, $R_6$, $R_7$, $R_8$, $R_9$, $R_{10}$, $R_{11}$, $R_{12}$, $R_{13}$ and $R_{14}$ are each independently hydrogen, halogen, alkyl or phenyl;

$n_1$, $n_2$, $n_3$, $n_4$ and $n_5$ are each independently 0 or 1;

with the proviso that if $R_4$ and $R_{15}$ together are $-(CH_2)_m-$, the sum of $n_1$, $n_2$, $n_3$, $n_4$, $n_5$ and m is 2 or 3.

The term "halogen", as used throughout the specification, refers to fluorine, chlorine, bromine and iodine.

The terms "alkyl" and "alkoxy", as used throughout the specification, refer to groups having 1 to 5 carbon atoms.

DETAILED DESCRIPTION OF THE INVENTION

The compounds of formula I can be prepared by reacting a 2-sulfamoylaniline having the structural formula

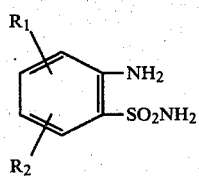

with a carbonyl derivative (or an acetal or ketal derivative thereof) having the structural formula

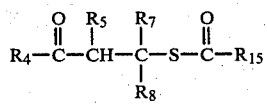

or an acetal or ketal having the structural formula

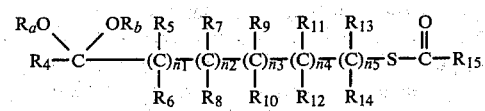

wherein $R_a$ and $R_b$ are each alkyl or together they are $-CH_2-CH_2-$ or $-CH_2-CH_2-CH_2-$. The reaction is conveniently run in an organic solvent, and proceeds most readily under reflux conditions.

Variations of the above process for ring closure of a 2-sulfamoylaniline are known in the art; see, for example, Angew. Chem. Internat. Edit. 1(5):235(1962) and Kirk-Othmer, Encyclopedia of Chem. Tech. Third Ed., 8, 1 (1977), Wiley, New York. Processes for the preparation of 2-sulfamoylanilines are also described in these references.

The starting materials of formula III can be prepared by reacting an α, β-unsaturated aldehyde or ketone having the formula

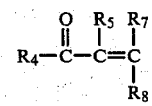

with the appropriate thiol acid having the formula

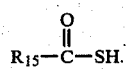

The above reaction is described in J. Chem. Soc. 2123 (1951) and Houben-Weyl, Ketones, Part III, 2401, 1977, G. Thieme Verlag, Stuttgart, 1977.

The starting materials of formula IV can be prepared by acylating a mercapto acetal or ketal having the formula

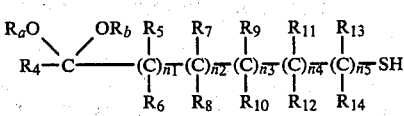

with an acid (or corresponding acid halide or acid anhydride) having the formula

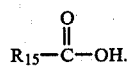

The above reaction is described in Houben-Weyl, Sulfur Compounds, Vol. IX, 749, G. Thieme Verlag, Stuttgart, 1955.

The compounds of formula I are useful therapeutic agents in mammalian species. They promote the urinary excretion of water and sodium ion. As diuretics, they are useful in the treatment of edematous states, e.g., edematous states associated with renal dysfunction, with congestive heart failure, and with other disease states. They are also useful in the treatment of hypertension.

The diuretics of formula I may be incorporated in a conventional dosage form such as tablet, capsule, elixir, injectable or the like, along with the necessary carrier material, excipient, lubricant, buffer or the like.

Preferred compounds of formula I are those wherein $R_1$ is aminosulfonyl, $R_3$ is hydrogen, $R_4$ is hydrogen and $n_4$ and $n_5$ are O.

The following examples are specific embodiments of this invention.

EXAMPLE 1

3-[2-(Acetylthio)ethyl]-6-chloro-3,4-dihydro-2H-1,2,4-benzothiadiazine-7-sulfonamide, 1,1-dioxide (A) β-Acetylmercaptopropanal To 13.4 ml of acrolein cooled by an ice bath, there is added in 1 ml portions 14.2 ml of thioacetic acid. After standing for 1 hour, the product is fractioned at 94°–96° C./14 mm of Hg to yield an oil.

(B) 3-[2-(Acetylthio)ethyl]-6-chloro-3,4-dihydro-2H-1,2,4-benzothiadiazine-7-sulfonamide, 1,1-dioxide A mixture of 11.4 g of 2,4-disulfamoyl-5-chloroaniline, 10.6 g β-acetylmercaptopropanal and 200 ml of acetonitrile is refluxed for 24 hours. The resulting solution is evaporated and the remaining oil is washed with three 50 ml portions of petroleum ether and then dissolved in about 50 ml of ethyl acetate; a solid separates and is filtered off (3.9 g). The filtrate is slowly poured into toluene to furnish a sticky solid (8.2 g). On standing the combined petroleum ether washes yield 0.8 g of solid.

A sample of the 3.9 g fraction is crystallized from hot isoamyl formate yielding the title compound, melting point 192°–195° C.

Analysis calc'd for $C_{11}H_{14}Cl_3N_5O_3S$: C, 33.04; H, 3.53; N, 10.51; Found: C, 33.17; H, 3.60; N, 10.38.

EXAMPLE 2

3-[2-(Acetylthio)ethyl]-6-trifluoromethyl-3,4-dihydro-2H-1,2,4-benzothiadiazine-7-sulfonamide, 1,1-dioxide Following the procedure of Example 1, but substituting 2,4-disulfamoyl-5-trifluoromethyl aniline for 2,4-disulfamoyl-5-chloroaniline, the title compound is obtained.

EXAMPLE 3

3-[3-(Acetylthio)propyl]-6-nitro-3,4-dihydro-2H-1,2,4-benzothiadiazine-7-sulfonamide, 1,1-dioxide Following the procedure of example 1, but substituting γ-acetylmercaptobutanal for β-acetylmercaptopropanal and 2,4-disulfamoyl-5-nitroaniline for 2,4-disulfamoyl-5-chloroaniline, yields the title compound.

EXAMPLE 4

3-[2-(Acetylthio)ethyl]-3-methyl-6-chloro-3,4-dihydro-2H-1,2,4-benzothiadiazine-7-sulfonamide-1,1-dioxide (A) Acetylthioacetone Triethylamine (10 g) is added with stirring at 0° C. to a solution of 7.6 g of thiolacetic acid in 180 ml of ether. To the resulting mixture is added 9.2 g of chloroacetone at 5°–10° C., and the mixture is then refluxed for 90 minutes. The mixture is cooled, filtered and the filtrate evaporated. The residue is distilled; boiling point 57°–58° C. at 0.1 mm of Hg.

(B) Acetylthioacetone, dimethyl ketal

A mixture of 6.5 g of acetylthioacetone, 10 g of methyl orthoformate, 14 ml of methanol and 0.1 ml of concentrated hydrochloric acid is kept at room temperature overnight. The solvent is evaporated and the residue is distilled; boiling point 57°–59° C. at 0.1 mm of Hg.

(C) 3-[2-(Acetylthio)ethyl]-3-methyl-6-chloro-3,4-dihydro-2H-1,2,4-benzothiadiazine-7-sulfonamide-1,1-dioxide Following the procedure of example 1B, but substituting acetylthioacetone, dimethyl ketal for β-acetylmercaptopropanal, yields the title compound.

What is claimed is:

1. A compound having the formula

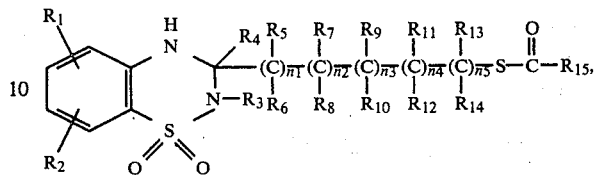

wherein $R_1$ and $R_2$ are each independently hydrogen, halogen, trifluoromethyl, aminosulfonyl, nitro, alkyl or alkoxy;

$R_3$ is hydrogen, alkyl, or phenylmethyl;

$R_4$ is hydrogen, alkyl, or phenyl, and $R_{15}$ is alkyl, phenyl or phenylmethyl, or $R_4$ and $R_{15}$ together are $-(CH_2)_m-$ wherein m is 1 or 2;

$R_5$, $R_6$, $R_7$, $R_8$, $R_9$, $R_{10}$, $R_{11}$, $R_{12}$, $R_{13}$ and $R_{14}$ are each independently hydrogen, halogen, alkyl or phenyl;

$n_1$, $n_2$, $n_3$, $n_4$, and $n_5$ are each independently O or 1;

with the proviso that if $R_4$ and $R_{15}$ together are $-(CH_2)_m-$, the sum of $n_1$, $n_2$, $n_3$, $n_4$, $n_5$ and m is 2 or 3.

2. A compound in accordance with claim 1 wherein $R_1$ is aminosulfonyl.

3. A compound in accordance with claim 1 wherein $R_3$ is hydrogen.

4. A compound in accordance with claim 1 wherein $R_4$ is hydrogen.

5. A compound in accordance with claim 1 wherein $n_4$ and $n_5$ are O.

6. A compound in accordance with claim 1 having the formula

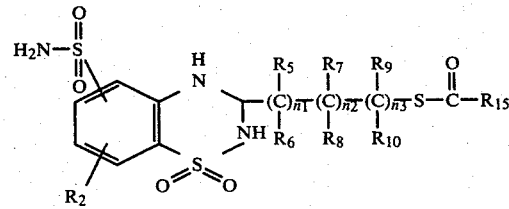

7. A compound in accordance with claim 6 having the formula

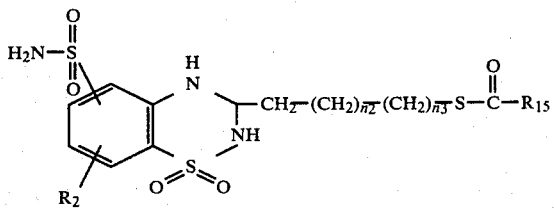

8. The compound in accordance with claim 1, 3-[2-(acetylthio)ethyl]-6-chloro-3,4-dihydro-2H-1,2,4-benzothiadiazine-7-sulfonamide, 1,1-dioxide.

9. The compound in accordance with claim 1, 3-[2-(acetylthio)ethyl]-3-methyl-6-chloro-3,4-dihydro-2H-1,2,4-benzothiadiazine-7-sulfonamide, 1,1-dioxide.

* * * * *